United States Patent [19]
Herrmann et al.

[11] Patent Number: 5,710,292
[45] Date of Patent: Jan. 20, 1998

[54] PROCESS FOR THE SELECTIVE OXIDATION OF AROMATIC COMPOUNDS

[75] Inventors: Wolfgang Anton Herrmann, Freising; Joao Domingos Galamba Correia, München; Richard Walter Fischer, Frankfurt, all of Germany

[73] Assignee: Hoechst Aktiengesellschaft, Frankfurt, Germany

[21] Appl. No.: 459,836

[22] Filed: Jun. 2, 1995

[30] Foreign Application Priority Data

Jun. 6, 1994 [DE] Germany .................. P 44 19 800.0

[51] Int. Cl.⁶ .................. C07C 50/12; C07C 52/32; C07C 27/10; C07C 27/16
[52] U.S. Cl. .................. 552/296; 552/299; 568/910
[58] Field of Search .................. 552/296, 299; 568/955, 910

[56] References Cited

U.S. PATENT DOCUMENTS

| | | | |
|---|---|---|---|
| 3,316,279 | 4/1967 | Fenton . | |
| 3,518,285 | 6/1970 | Fenton . | |
| 4,973,718 | 11/1990 | Buchler et al. | 549/531 |
| 4,987,226 | 1/1991 | Buchler et al. | 540/145 |
| 5,155,247 | 10/1992 | Herrmann et al. | 556/46 |
| 5,166,372 | 11/1992 | Crocco et al. | 549/531 |

FOREIGN PATENT DOCUMENTS 0508385  10/1992  European Pat. Off. .

OTHER PUBLICATIONS

Adam et al. "Homogeneous Catalytic Oxidation Of Arenes and a New Synthesis of Vitamin K3", Angew. Chem. vol. 33 (23/24), pp. 2475–2477, 1994.

Bull. Chem. Jp vol. 62; No. 5; 1989.

Abstract of EP 0,665,209. 1995.

Adam et al. "Homogeneous Catalytic Oxidation of Arenes and a New Synthesis of Vitamin K₃", Angew. Chem. vol. 33 (23/24), pp. 2475–2477, Jan. 3, 1995 [English Version].

Adam et al. "Homogeneous Catalytic Oxidation of Arenes and a New Synthesis of Vitamin K₃", Angew. Chem. vol. 33 (23/24), pp. 2475–2477, Dec. 19, 1994 [German Version].

*Primary Examiner*—José G. Dees
*Assistant Examiner*—Barbara Badio
*Attorney, Agent, or Firm*—Curtis Morris & Safford P.C

[57] ABSTRACT

The invention relates to the use of compounds of the formula $$Re_aO_bX_cL_d \qquad (I)$$

in which

X=F, Cl, Br, I or OH,

L=Lewis base, a=an integer 1, 2 or 3 b=zero or an integer from 2 to 9, c=zero or an integer from 1 to 9, d=zero or an integer from 1 to 6, and the sum of a, b and c is such that it is appropriate to the zerovalency or trivalency to heptovalency of the rhenium with the proviso that if b is not equal to zero, b≧2·a, as catalysts for the oxidation of electron-rich aromatic compounds and derivatives thereof and a process for the oxidation of electron-rich aromatic compounds, in which electron-rich $C_6$–$C_{22}$ aryl compounds and derivatives thereof are oxidized in an organic solvent in the presence of a catalyst of the formula (I) and of a peroxide-containing compound.

20 Claims, No Drawings

PROCESS FOR THE SELECTIVE OXIDATION OF AROMATIC COMPOUNDS

Oxidation is the most important type of reaction in organic synthesis. Numerous base chemicals and fine chemicals result from oxidative processes which frequently make use of atmospheric oxygen, hydrogen peroxide and organic peroxides as oxidizing agents. In many cases efficient, selective reactions only occur if these oxidizing agents are used in the presence of catalysts. These catalysts are generally metal oxides, for example $V_2O_5$, $CrO_3$, $MoO_3$, $WO_3$, $OsO_4$ and $RuO_4$. Oxometallates such as chromate and permanganate are also occasionally found as oxidizing agents. The said catalysts display high efficiency in epoxidation, hydroxylation and carboxylation reactions on olefins (H. A. Jergensen, Chem. Rev. 1989, Vol. 89, pp. 431–458).

However, use of such systems for the catalytic oxidation of aromatic compounds is subject to many restrictions. Insufficient activity ($WO_3$) on the one hand and deficient selectivity on the other hand ($CrO_3/H_2SO_4$) in addition to the fact that safety with respect to ecology, health or pharmacology is frequently not ensured (e.g. in the case of $CrO_3$ or $OsO_4$) have hindered hitherto the industrial use of such catalysts.

Other processes established in oxidation chemistry, which, e.g. employ electrochemical oxidation, cerium (IV) salts, manganese (III) sulfate or peracids or peroxides (t-BuOOH) in the presence of molybdenum complexes as oxidizing agents, in the oxidation of simple or condensed aromatics or derivatives thereof prove to be highly complex, expensive, frequently burdened with high salt loadings through the stoichiometric use required (cerium (IV) salts, manganese (III) sulfate) and generally also unspecific (R. P. Kreh et al., Org. Chem., 1989, 54, 1526–1531; M. Hudlicky, Oxidations in Organic Chemistry, ACS Monograph 186, Washington/DC, 1990, S. 92–98; T. A. Gorodetskaya et al., U.S.S.R. Patent 1 121 255, 1984; Chem. Abstr., 1985, 102, 203754; W. Adam et al., Synthesis, 1993, 280–282, J. Skarzewski, Tetrahedron, 1984, 40, 4997–5000; S. Yamaguchi et al., Bull. Chem. Soc. Jpn., 1986, 59, 2881–2884; M. Periasamy, M. V. Bhatt, Tetrahedron Lett. 1978, 4561–4562; Y. Asakawa et al., 1988, J. Org. Chem., 53, 5453–5457; W. Chen, Chem. Abstr., 1987, 17, 58620).

Work by Buchler et al. (DE-A-3731689, DE-A-3731690) has shown that rhenium complexes epoxidize olefins but not aromatics.

EP-A-380085 discloses organorhenium compounds which are used as catalysts for the oxidation of olefins in the presence of hydrogen peroxide. It was established here that other rhenium compounds, namely $Re_2O_7$, $ReO_3$, $ReO_2$ and $(CH_3)_3SnOReO_3$ do not display any catalytic activities in the target oxidation of olefins.

The German Application (P 4402333.2) which has an earlier priority but which had not been published at the date of filing of the present application dicloses organorhenium oxides which can be effectively used as selective catalysts for the oxidation of a multiplicity of aromatic compounds to give quinoid systems in the presence of peroxide-containing reagents.

It is a disadvantage that the catalyst must be prepared from simpler rhenium compounds before use which implies taking up a certain amount of time and additional costs.

The object is therefore to find a storable, active catalyst system which is accessible as easily as possible, inexpensive and can be handled easily which achieves the desired selectivity in the oxidation of aromatics.

The invention relates to the use of compounds of the formula $$Re_aO_bX_cL_d \qquad (I)$$

in which

X=F, Cl, Br, I or OH,
L=Lewis base,
a=an integer 1, 2 or 3
b=zero or an integer from 2 to 9,
c=zero or an integer from 1 to 9,
d=zero or an integer from 1 to 6, and the sum of a, b and c is such that it is appropriate to the zerovalency or trivalency to heptovalency of rhenium with the proviso that if b is not equal to zero, b≧2·a, as catalysts for the oxidation of electron-rich aromatic compounds and derivatives thereof.

Examples of the Lewis base L are pyridine, bipyridine, t-butylpyridine, amines, in particular secondary and tertiary amines such as triethylamine and quinuclidine, $H_2O$ and polyethers such as diglyme.

Preferably, compounds are used in which b is an integer from 2 to 9, c is zero or 1 and X, L, a and d have the abovementioned meanings.

Particularly preferably, the rhenium oxides $ReO_2$, $ReO_3$ and $Re_2O_7$, rhenium trioxofluoride ($FReO_3$) and rhenium trioxochloride ($ClReO_3$) and their corresponding Lewis-base L-adducts are used.

Very particular preference is given to $ReO_3$ and $Re_2O_7$.

The invention further relates to a process for the oxidation of electron-rich aromatic compounds which comprises oxidizing in an organic solvent electron-rich $C_6$–$C_{22}$-aryl compounds and derivatives thereof in the presence of a catalyst of the formula $Re_aO_bX_cL_d$ (I), in which X, L, a, b, c and d have the abovementioned meanings, and of a peroxide-containing compound.

Suitable aryl compounds for the process according to the invention are electron-rich aromatic compounds or condensed aromatic systems having 6 to 22 carbon atoms, preferably having 6 to 14 carbon atoms, which if appropriate can be monosubstituted or polysubstituted, identically or differently, by an electron-donor group. Typical suitable electron-donor groups are hydroxyl, $C_1$–$C_3$-alkoxy, N-acylamino, N-acylamino-$C_1$–$C_3$-alkyl, acyloxy- and $C_1$–$C_3$-alkyl.

Examples of such aryl compounds are xylenes, disubstituted, trisubstituted or tetrasubstituted $C_1$–$C_3$-alkylbenzenes or $C_1$–$C_3$-alkoxybenzenes, naphthalene and monosubstituted to hexasubstituted $C_1$–$C_3$-alkyl or $C_1$–$C_3$-alkoxy derivatives thereof, anthracene and $C_1$–$C_3$-alkyl or $C_1$–$C_3$-alkoxy derivatives thereof, phenanthrene and higher condensed aromatics, phenol, hydroquinone, resorcinol pyrocatechol and pyrogallol, but also biphenyl.

Preferred aryl compounds are naphthalene and anthracene and derivatives thereof, particular preference is given to naphthalene and derivatives thereof, in particular 2-methylnaphthalene.

By means of the process according to the invention, the aryl compounds are generally oxidized to the corresponding quinoid systems. From 2-methylnaphthalene, for example, is obtained 2-methyl-1,4-naphthoquinone, the parent substance of the vitamin K series.

In the case of higher-substituted (trisubstituted and above) aryl compounds in which the formation of a quinoid system is not possible, by means of the process according to the invention the corresponding hydroxyl compound is prepared. Typical examples of such higher-substituted aryl compounds are 1,2,3,5,8-pentamethylnaphthalene; 1,2,3-trimethylbenzene, mesitylene and 1,3,5-trimethoxybenezene. From these starting materials are obtained, for example, by the process according to the invention the following hydroxyl compounds: 4-hydroxy-1, 2,3,5,8-pentamethylnaphthalene, 1-hydroxy-3,4,5-trimethylbenzene, 1-hydroxy-2,4,6-trimethylbenzene and 1-hydroxy-2,4,6-trimethoxybenzene.

In accordance with the process according to the invention, the aromatic compound to be oxidized is dissolved in an organic solvent and the catalyst is added. The concentration of the dissolved aromatic compounds is 0.1 mol in 10–1000 ml, preferably 0.1 mol in 25–250 ml, particularly preferably 0.1 mol in 50–200 ml of solvent. Suitable organic solvents are for example glacial acetic acid, THF, tert-butanol or tert-butyl methyl ether, preferably glacial acetic acid or THF. The catalyst can be used in an amount of 0.01–10.0 mol %, preferably 0.1–2.0 mol %. To this solution is added the peroxide-containing compound (5–90% by weight) in a molar ratio of 1:1 to 20:1, based on the aromatic compounds to be oxidized.

The reaction is substantially pH-independent; preferably, the reaction is carried out at pH≦7.

The reaction mixture is stirred at a temperature of 10°–100° C., preferably 20°–70° C., until reaction is complete. The reaction mixture is then worked up in a manner usual for those skilled in the art, i.e. for example neutralized, extracted and dried. The crude oxidation product can be further purified, for example by high-vacuum distillation or by recrystallization.

The rhenium compounds of the formula I are commercially available as commercial grade compounds (ReO$_2$, ReO$_3$, Re$_2$O$_7$) or may easily be prepared (G. Brauer, Handbuch der Präparativen Anorganischen Chemie, [Handbook of Preparative Inorganic Chemistry], 3rd Edition, Enke-Verlag, Stuttgart 1981). However, their suitability as oxidation catalyst of aromatics is novel and was in no way to be expected (EP-A-380085). Their particular advantage is that they are generally commercially available, nonvolatile and substantially pH-independent and may be separated off in a simple manner from the oxidation system. The compounds of the formula I in combination with peroxide-containing compounds, such as hydrogen peroxide, inorganic peroxides, e.g. alkali metal peroxides, in particular sodium peroxide, and percarboxylic acids and salts thereof such as m-chloroperbenzoic acid, peracetic acid and magnesium monoperoxonaphthalate, are highly active catalysts for the oxidations according to the invention.

Particularly preferably, the compounds of the formula I are used in combination with hydrogen peroxide, the concentration of which can be in the range of 5–90%, preferably 60–85%. Commercial grade Perhydrol (=30% strength H$_2$O$_2$) can also be used.

Examples

General procedural instructions for the rhenium-catalyzed oxidation of aromatic compounds.

The substrates to be oxidized were dissolved in glacial acetic acid, THF or mixtures thereof and the catalyst was added. Finally, hydrogen peroxide was added as oxidizing agent. The reaction mixture was stirred at 20°, 40° or 70° C. (see Table) until reaction was complete.

Work-up:

The reaction solution was neutralized using a saturated sodium hydrogen carbonate solution. The aqueous mother liquor was extracted three times using methylene chloride; the combined extracts were dried over MgSO$_4$. The solvent was then removed in vacuo. After removal of the methylene chloride, generally yellow, solid oxidation products were obtained. The examples carried out in accordance with the above procedural instructions are to be taken from Table 1.

TABLE 1

Oxidation examples according to the general procedural instructions with associated reaction conditions

| No. | Aryl compound (10 mmol in each case) | Catalyst (0.2 mmol in each case) | t [h] | T [°C.] | Solvent | Yield (% by weight) | Product |
|---|---|---|---|---|---|---|---|
| 1 | 2,3-dimethylnaphthalene | ReO$_3$[f] | 4 | 20 | AcOH/THF[a] | 30 | 2,3-dimethylnaphthoquinone |
| 2 | 2,3-dimethylnaphthalene | Re$_2$O$_7$.bipyridine[∞] | 4 | 20 | AcOH/THF[a] | 43 | 2,3-dimethylnaphthoquinone |
| 3 | 2,3-dimethylnaphthalene | FReO$_3$.bipyridine[∞] | 4 | 20 | AcOH/THF[a] | 11 | 2,3-dimethylnaphthoquinone |
| 4 | 2,3-dimethylnaphthalene | ClReO$_3$.bipyridine[∞] | 4 | 20 | AcOH/THF[a] | 74 | 2,3-dimethylnaphthoquinone |
| 5 | 2,3-dimethylnaphthalene | BrReO$_3$.bipyridine[∞] | 4 | 20 | AcOH/THF[a] | 5 | 2,3-dimethylnaphthoquinone |
| 6 | 2,3-dimethylnaphthalene | C$_6$H$_{14}$N$_3$ReO$_3$ReO$_4$[∞] | 4 | 20 | AcOH/THF[a] | 11 | 2,3-dimethylnaphthoquinone |
| 7 | 2,3-dimethylnaphthalene | ReO$_3$[∞] | 24 | 20 | THF[b] | 43 | 2,3-dimethylnaphthoquinone |
| 8 | 2,3-dimethylnaphthalene | Re$_2$O$_7$[∞] | 24 | 20 | THF[b] | 51 | 2,3-dimethylnaphthoquinone |
| 9 | 2,3-dimethylnaphthalene | ClReO$_3$[∞] | 4 | 20 | THF[b] | 23 | 2,3-dimethylnaphthoquinone |
| 10 | 2,3-dimethylnaphthalene | ClReO$_3$.bipyridine[∞] | 5 | 20 | THF[b] | 36 | 2,3-dimethylnaphthoquinone |
| 11 | Mesitylene | ReO$_3$[∞] | 4 | 20 | AcOH[c] | 69 | 4-hydroxymesitylene |
| 12 | mesitylene | Re$_2$O$_7$[∞] | 4 | 20 | AcOH[c] | 14 | 4-hydroxymesitylene |
|  |  |  |  |  |  | 37 | 1,3-dihydroxymesitylene |
| 13 | mesitylene | Re$_2$O$_7$[f] | 2 | 40 | AcOH[c] | 73 | 4-hydroxymesitylene |
| 14 | mesitylene | Re$_2$O$_7$[e] | 1 | 20 | AcOH[c] | 38 | 4-hydroxymesitylene |
| 15 | 1,2,3-trimethylbenzene | Re$_2$O$_7$[f] | 0.17 | 70 | AcOH[c] | 34 | 3,4,5-trimethylphenol |

TABLE 1-continued

Oxidation examples according to the general procedural instructions with associated reaction conditions

| No. | Aryl compound (10 mmol in each case) | Catalyst (0.2 mmol in each case) | t [h] | T [°C.] | Solvent | Yield (% by weight) | Product |
|---|---|---|---|---|---|---|---|
| 16 | 1,3,5-trimethoxy-benzene | Re$_2$O$_7$ $^{\theta)}$ | 1 | 20 | AcOH$^{c)}$ | 20 | 2,4,6-trimethoxy-phenol |
| 17 | 2-methylnaphthalene | Re$_2$O$_7$ $^{\delta)}$ | 4 | 20 | AcOH$^{c)}$ | 57 | 2-methylnaphthoquinone |
| 18 | 2-methylnaphthalene | Re$_2$O$_7$ $^{\eta)}$ | 4 | 20 | AcOH$^{c)}$ | 33 | 2-methylnaphthoquinone |
| 19 | 2-methylnaphthalene | Re$_2$O$_7$ $^{\eta)}$ | 4 | 40 | AcOH$^{c)}$ | 57 | 2-methylnaphthoquinone |
| 20 | 2-methylnaphthalene | Re$_2$O$_7$ $^{\delta)}$ | 4 | 40 | AcOH$^{c)}$ | 70 | 2-methylnaphthoquinone |

$C_6H_{14}N_3$ = 1,3,7-triazacyclononane
Solvent:
$^{a)}$22 ml AcOH + THF (THF quantity sufficient for complete dissolution of the substrate after addition of H$_2$O$_2$)
$^{b)}$22 ml THF
$^{c)}$22 ml AcOH (= glacial acetic acid);
85% H$_2$O$_2$; molar ratio of aryl compound/H$_2$O$_2$ = $\alpha$) 1:20, $\beta$) 1:15, $\gamma$) 1:10, $\delta$) 1:7, $\epsilon$) 1:5, $\eta$) 1:3, $\theta$) 1:1

We claim:

1. A method of using compounds of the formula (I) as catalysts for the oxidation of electron-rich aromatic compounds and derivatives thereof, wherein the formula (I) is:

$$Re_aO_bX_cL_d \quad (I)$$

in which
X=F, Cl, Br, I or OH,
L=Lewis base,
a=an integer 1, 2 or 3,
b=zero or an integer from 2 to 9,
c=zero or an integer from 1 to 9,
d=zero or an integer from 1 to 6,
and the sum of a, b and c is such that it is appropriate to the zerovalency or trivalency to heptovalency of rhenium with the proviso that if b is not equal to zero, b≧2·a, comprising the steps of adding the aromatic compounds and catalyst to a solvent and oxidizing the aromatic compounds at the aromatic core.

2. A method as claimed in claim 1, wherein b is an integer from 2 to 7 and c is zero or 1.

3. A process for oxidizing in an organic solvent electron-rich $C_6$–$C_{22}$-aryl compounds and derivatives thereof comprising the step of oxidizing the $C_6$–$C_{22}$-aryl compounds in the presence of a catalyst of the formula $Re_aO_bX_cL_d$ (I), in which
X=F, Cl, Br, I or OH,
L=Lewis base,
a=an integer 1, 2 or 3,
b=zero or an integer from 2 to 9,
c=zero or an integer from 1 to 9,
d=zero or an integer from 1 to 6,
and the sum of a, b and c is such that it is appropriate to the zerovalency or trivalency to heptovalency of rhenium with the proviso that if b is not equal to zero, b≧2·a, and of a peroxide-containing compound and wherein said $C_6$–$C_{22}$-aryl compounds are oxidized at the aromatic core.

4. The process as claimed in claim 3, wherein the peroxide-containing compound used is hydrogen peroxide.

5. The process as claimed in claim 3, wherein a $C_6$–$C_{14}$-aryl compound is oxidized.

6. The process as claimed in claim 3, wherein naphthalene and derivatives thereof are oxidized.

7. The process as claimed in claim 3, wherein 2-methylnaphthalene is oxidized.

8. The method as claimed in claim 1, wherein the said aromatic compounds comprise $C_6$–$C_{22}$-aryl compounds.

9. The method as claimed in claim 1, wherein said aromatic compounds comprise $C_6$–$C_{14}$-aryl compounds.

10. The method as claimed in claim 1, wherein said aromatic compounds are selected from the group consisting of naphthalene and derivatives thereof.

11. The method as claimed in claim 1, wherein said aromatic compounds comprise 2-methylnaphthalene.

12. The method as claimed in claim 1, wherein the catalysts are selected from the group consisting of ReO$_2$, ReO$_3$, Re$_2$O$_7$, FReO$_3$, ClReO$_3$ and the corresponding Lewis-base L-adducts thereof.

13. The method as claimed in claim 1, wherein the catalysts comprise ReO$_3$, Re$_2$O$_7$, or mixtures thereof.

14. The method as claimed in claim 1, wherein said aromatic compounds are aryl compounds and said aryl compounds are oxidized to the corresponding quinoid systems.

15. The method as claimed in claim 1, wherein said aromatic compounds are aryl compounds and said aryl compounds are oxidized to the corresponding hydroxyl systems.

16. The method as claimed in claim 1, wherein said aromatic compound is dissolved in an organic solvent and said catalyst is subsequently added to said organic solvent to form a reaction mixture and said aromatic compound is oxidized at the aromatic core.

17. The method as claimed in claim 16, wherein the concentration of the dissolved aromatic compounds in said reaction mixture is 0.2 mol in 10–1000 ml of solvent.

18. The method as claimed in claim 16, wherein said reaction mixture is stirred at a temperature of 10°–100° C.

19. The process as claimed in claim 3, wherein said aromatic compounds are aryl compounds and said aryl compounds are oxidized to the corresponding hydroxyl systems.

20. The process as claimed in claim 3, wherein said oxidized aryl compounds are subsequently extracted and dried.

* * * * *